(12) United States Patent
Kawahara et al.

(10) Patent No.: US 12,009,104 B2
(45) Date of Patent: Jun. 11, 2024

(54) MEDICAL IMAGE PROCESSING APPARATUS, MEDICAL IMAGE PROCESSING METHOD, MACHINE LEARNING SYSTEM, AND PROGRAM

(71) Applicant: FUJIFILM Corporation, Tokyo (JP)

(72) Inventors: Misaki Kawahara, Kanagawa (JP); Goro Miura, Kanagawa (JP); Satoshi Naito, Kanagawa (JP); Shumpei Kamon, Kanagawa (JP); Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 757 days.

(21) Appl. No.: 17/117,408

(22) Filed: Dec. 10, 2020

(65) Prior Publication Data
US 2021/0125724 A1    Apr. 29, 2021

Related U.S. Application Data

(63) Continuation of application No. PCT/JP2019/022908, filed on Jun. 10, 2019.

(30) Foreign Application Priority Data

Jun. 28, 2018    (JP) .................... 2018-123441

(51) Int. Cl.
*G16H 50/70*    (2018.01)
*A61B 1/00*    (2006.01)
(Continued)

(52) U.S. Cl.
CPC ....... *G16H 50/70* (2018.01); *A61B 1/000096* (2022.02); *G06F 18/214* (2023.01);
(Continued)

(58) Field of Classification Search
CPC ........ G16H 50/70; G16H 50/20; G16H 30/40; G06N 20/00; G06V 10/774; G06V 10/776;
(Continued)

(56) References Cited

U.S. PATENT DOCUMENTS

2005/0010445 A1    1/2005    Krishnan et al.
2006/0018524 A1    1/2006    Suzuki et al.
(Continued)

FOREIGN PATENT DOCUMENTS

CN    108056789 A    5/2018
JP    2002-174603 A    6/2002
(Continued)

OTHER PUBLICATIONS

Communication pursuant to Article 94(3) EPC issued by the European Patent Office dated May 15, 2023, which corresponds to European Patent Application No. 19826063.0-1126 and is related to U.S. Appl. No. 17/117,408.
(Continued)

*Primary Examiner* — Michael R Neff
(74) *Attorney, Agent, or Firm* — Studebaker & Brackett PC (57) ABSTRACT

There are provided a medical image processing apparatus, a medical image processing method, a machine learning system, and a program that can reduce the volume of communication and can reduce the processing load of retraining or additional training that is performed by a machine learning apparatus. A medical image processing apparatus (13) includes: a trainer (26) that performs additional training for a first computer-aided diagnosis device on the basis of an input medical image; an evaluation unit that compares a second computer-aided diagnosis device obtained by the additional training with the first computer-aided diagnosis
(Continued)

device and evaluates whether learning difference information about the additional training contributes to improvement of performance of the first computer-aided diagnosis device; a communication determination unit that determines, on the basis of a result of evaluation, whether the learning difference information is to be communicated; and a communication unit (34) that outputs the learning difference information in accordance with a result of determination by the communication determination unit.

13 Claims, 8 Drawing Sheets

(51) Int. Cl.
| | |
|---|---|
| *G06F 18/21* | (2023.01) |
| *G06F 18/214* | (2023.01) |
| *G06N 20/00* | (2019.01) |
| *G06V 10/774* | (2022.01) |
| *G06V 10/776* | (2022.01) |
| *G16H 30/40* | (2018.01) |
| *G16H 50/20* | (2018.01) |

(52) U.S. Cl.
CPC ........... *G06F 18/217* (2023.01); *G06N 20/00* (2019.01); *G06V 10/774* (2022.01); *G06V 10/776* (2022.01); *G16H 30/40* (2018.01); *G16H 50/20* (2018.01)

(58) Field of Classification Search
CPC ............ A61B 1/000096; G06F 18/217; G06F 18/214
USPC ........................................................ 382/128
See application file for complete search history.

(56) References Cited

U.S. PATENT DOCUMENTS

| | | |
|---|---|---|
| 2010/0135552 A1 | 6/2010 | Leib et al. |
| 2013/0243244 A1 | 9/2013 | Miyamoto et al. |
| 2016/0148371 A1 | 5/2016 | Itu et al. |
| 2016/0259899 A1* | 9/2016 | Ludviksson ............ G16H 50/20 |
| 2017/0024641 A1 | 1/2017 | Wierzynski |
| 2018/0144209 A1 | 5/2018 | Kim et al. |
| 2019/0110753 A1* | 4/2019 | Zhang ..................... G16H 50/20 |

FOREIGN PATENT DOCUMENTS

| | | |
|---|---|---|
| JP | 2007-528746 A | 10/2007 |
| JP | 2013-192624 A | 9/2013 |
| JP | 2015-116319 A | 6/2015 |
| JP | 2017-187918 A | 10/2017 |
| WO | 2010050334 A1 | 5/2010 |
| WO | 2018/070285 A1 | 4/2018 |

OTHER PUBLICATIONS

The extended European search report issued by the European Patent Office dated Aug. 16, 2021, which corresponds to European Patent Application No. 19826063.0-1126 and is related to U.S. Appl. No. 17/117,408.
International Search Report issued in PCT/JP2019/022908, dated Sep. 3, 2019.
Non-Patent Literature: Medical Imaging Technology, Mar. 2014, vol. 32, No. 2, pp. 98-108, (Nomura, Yukihiro et al., Development, clinical use, continuous performance improvement of CAD software based on multi-institutional collaboration in teleradiology environment).
International Preliminary Report on Patentability and Written Opinion issued in PCT/JP2019/022908, dated Dec. 29, 2020.
An Office Action issued by the China National Intellectual Property Office dated Sep. 22, 2023, which corresponds to Chinese Patent Application No. CN 201980042852.8.

* cited by examiner

MEDICAL IMAGE PROCESSING APPARATUS, MEDICAL IMAGE PROCESSING METHOD, MACHINE LEARNING SYSTEM, AND PROGRAM

CROSS-REFERENCE TO RELATED APPLICATIONS

The present application is a Continuation of PCT International Application No. PCT/JP2019/022908 filed on Jun. 10, 2019 claiming priority under 35 U.S.C. § 119(a) to Japanese Patent Application No. 2018-123441 filed on Jun. 28, 2018. Each of the above applications is hereby expressly incorporated by reference, in its entirety, into the present application.

BACKGROUND OF THE INVENTION

1. Field of the Invention

The present invention relates to a medical image processing apparatus, a medical image processing method, a machine learning system, and a program and specifically relates to a machine learning technique to be applied to computer-aided diagnosis (CAD).

2. Description of the Related Art

In medical practice, medical image diagnosis, such as endoscopic diagnosis, ultrasonic diagnosis, X-ray image diagnosis, or a CT (computerized tomography) image diagnosis, is of high importance. For example, as described in WO2010/050334A1, JP2007-528746A, and JP2015-116319A, in a CAD system that analyzes a medical image using a computer to support diagnosis, an image recognition method using machine learning is used.

WO2010/050334A1 describes a medical image system including a classifier that performs classification for determining an image-captured area in a medical image. The classifier is configured by using a machine learning method. The medical image system described in WO2010/050334A1 is configured to compare the performance of an existing classifier with the performances of one or more new classifiers and to perform switching to a classifier having a highest determination accuracy. The term "classifier" is a synonym of "recognizer".

JP2007-528746A describes a CAD system that automatically detects a problematic area in a medical image and displays the detected problematic area with a mark. The CAD system described in JP2007-528746A includes a learning engine and performs machine learning for improving a knowledge base, such as a classification model, used in a process for detecting a problematic area.

JP2015-116319A describes a diagnosis support apparatus having a function of updating diagnosis knowledge using case data that includes medical images and a function of classifying case data using the diagnosis knowledge. The "diagnosis support apparatus" described in JP2015-116319A is understood as a term corresponding to a CAD apparatus.

SUMMARY OF THE INVENTION

In a machine learning apparatus that performs, for example, deep learning of images, learning data needs to be collected for the machine learning apparatus to create a recognition processing unit. Here, a large amount of good-quality learning data is necessary for learning. Accordingly, in a case of medical images, for example, a system is configured in which learning data is separately collected from edge devices in a plurality of hospitals in each of which one or more edge devices are installed, each of the edge devices having an image storage unit for storing medical images newly created in the hospital as data used in learning. That is, learning data is created by each of the plurality of edge devices on the basis of newly obtained medical images, and the learning data created by each edge device is sent to, for example, a facility outside the hospital for aggregation.

In a system outside the hospital, the accuracies of a large number of pieces of learning data thus collected are evaluated, teaching data is created by a teaching image creation unit, and a CAD module is created by using a machine learning apparatus. The CAD module may be a program module used in a recognition processing unit of the CAD system. The term "CAD module" may be replaced by a term, such as "CAD apparatus", "recognition model", or "recognizes".

In a case of a mechanism as described above, in order to perform, in the machine learning apparatus by batch, a learning process of relearning or additional learning of learning images collected from each edge device having the image storage unit, an excessively large processing capacity and an excessively long time are required. The volume of communication of learning data to be transmitted from each edge device to the system outside the hospital via a communication line becomes excessively large.

The present invention has been made in view of the above-described circumstances, and an object thereof is to provide a medical image processing apparatus, a medical image processing method, a machine learning system, and a program that can reduce the volume of communication and can reduce the processing load of retraining or additional training that is performed in a machine learning apparatus.

To address the issues, the following aspects of the invention are provided.

A medical image processing apparatus according to a first aspect includes: a trainer that performs additional training for a first computer-aided diagnosis device on the basis of an input medical image; an evaluation unit that compares a second computer-aided diagnosis device obtained by the additional training using the trainer with the first computer-aided diagnosis device and evaluates whether learning difference information about the additional training contributes to improvement of performance of the first computer-aided diagnosis device; a communication determination unit that determines, on the basis of a result of evaluation by the evaluation unit, whether the learning difference information is to be communicated; and a communication unit that outputs the learning difference information in accordance with a result of determination by the communication determination unit.

According to the first aspect, the trainer is installed in the medical image processing apparatus, additional training is performed for the first computer-aided diagnosis device in the medical image processing apparatus by using the input medical image, and the effect of the additional training is evaluated. As a result, the learning difference information served as good-quality learning data that can contribute to improvement of the performance of the first computer-aided diagnosis device can be selectively communicated. According to the first aspect, output, through communication, of data that does not contribute to performance improvement or data for which the degree of contribution is very small can be suppressed. Accordingly, useless signal processing can be reduced, and the volume of communication can be reduced.

Further, in the external information processing apparatus that receives the learning difference information output from the medical image processing apparatus according to the first aspect to collect data, the load of a process for creating learning data can be reduced, and the processing load of retraining or additional training performed in the external apparatus can be reduced.

The "additional training" means training that is additionally performed in order to update the performance of computer-aided diagnosis attained by already performed training. The "additional training" may be performed as batch training or may be performed as online training. The online training is a synonym of sequential training.

The medical image processing apparatus may be formed of a single apparatus or may be formed of a combination of a plurality of apparatuses. For example, the medical image processing apparatus can be implemented by using one or more computers. The term "apparatus" covers the concepts of "system" and "module". The term "data" covers the concepts of "information" and "signal".

The "medical image" may be an endoscopic image, a CT image, an X-ray image, an ultrasonic diagnosis image, an MRI (magnetic resonance imaging) image, a PET (positron emission tomography) image, a SPECT (single photon emission computed tomography) image, a fundus image, or an image of any other type.

In a second aspect, the medical image processing apparatus of the first aspect may be configured to further include: a feature value extraction unit that outputs feature value information about the medical image; and a recognition processing unit that performs a recognition process on the basis of the feature value information, in which the trainer performs the additional training on the basis of the feature value information and a result of recognition by the recognition processing unit.

The term "recognition" covers the concepts of, for example, classification, determination, inference, estimation, detection, and area extraction. The term "recognition processing unit" covers the concepts of, for example, recognizers, classifiers, determiners, detectors, and recognition models. The "recognition model" is a trained model that attains a certain level of recognition performance by machine learning. The recognition model may be understood as a program module that performs the recognition process.

In a third aspect, the medical image processing apparatus of the first or second aspect may be configured to further include a first information storage unit that stores parameter information about the first computer-aided diagnosis device.

In a fourth aspect, the medical image processing apparatus of any one of the first to third aspects may be configured in which the learning difference information includes parameter difference information that indicates a difference between parameter information about the first computer-aided diagnosis device and parameter information about the second computer-aided diagnosis device.

According to the fourth aspect, the volume of communication can be further reduced.

In a fifth aspect, the medical image processing apparatus of any one of the first to third aspects may be configured in which the learning difference information includes parameter information about the second computer-aided diagnosis device.

In a sixth aspect, the medical image processing apparatus of the second aspect may be configured in which the learning difference information includes the feature value information.

When the feature value information extracted from the medical image is used as learning data, the volume of communication can be reduced so as to be smaller than in a case where the medical image itself is communicated.

In a seventh aspect, the medical image processing apparatus of any one of the first to sixth aspects may be configured in which the learning difference information includes the medical image provided for the additional training.

In an eighth aspect, the medical image processing apparatus of any one of the first to seventh aspects may be configured in which the first computer-aided diagnosis device is a first recognizer that is created in advance by performing machine learning using a first learning dataset, and the second computer-aided diagnosis device is a second recognizer for which a parameter of the first recognizer is changed.

A machine learning system according to a ninth aspect includes: the medical image processing apparatus of any one of the first to eighth aspects; and an information processing apparatus that receives the learning difference information output from the communication unit to collect learning data including the learning difference information.

The medical image processing apparatus and the information processing apparatus can be connected to each other so as to enable communication. The term "connection" described here covers the concept of connection via a communication line. The term "connection" covers the concepts of both wired connection and wireless connection.

The machine learning system may be formed of a plurality of medical image processing apparatuses and at least one information processing apparatus. According to such an aspect, good-quality learning data can be efficiently collected from the plurality of medical image processing apparatuses.

In a tenth aspect, the machine learning system of the ninth aspect may be configured in which the information processing apparatus includes a training processing unit that uses the received learning difference information to perform a training process for the first computer-aided diagnosis device.

The information processing apparatus according to the tenth aspect functions as a machine learning apparatus. According to the tenth aspect, the processing load of retraining or additional training in the machine learning apparatus can be reduced.

In an eleventh aspect, in the machine learning system of the ninth or tenth aspect, the information processing apparatus further includes a second information storage unit that stores the received learning difference information.

The information processing apparatus in the eleventh aspect functions as a machine learning apparatus. According to the eleventh aspect, the processing load of retraining or additional training in the machine learning apparatus can be reduced.

A medical image processing method according to a twelfth aspect is a medical image processing method to be performed by a medical image processing apparatus, the medical image processing method including: a step of obtaining a medical image; a step of performing additional training for a first computer-aided diagnosis device by using a trainer on the basis of the obtained medical image; a step of comparing a second computer-aided diagnosis device obtained by the additional training using the trainer with the first computer-aided diagnosis device and evaluating whether learning difference information about the additional training contributes to improvement of performance of the first computer-aided diagnosis device; a step of determining, on the basis of a result of evaluation obtained in the evaluating, whether the learning difference information is to be communicated; and a step of outputting, from a communication unit, the learning difference information in accordance with a result of determination obtained in the determining.

In the medical image processing method of the twelfth aspect, matters the same as matters specified in the second to tenth aspects can be combined as appropriate. In this case, elements of the processing units or functional units that function as means responsible for the processes and operations specified in the configuration of the apparatus can be grasped as elements of corresponding steps of the processes and operations. The medical image processing method of the twelfth aspect may be understood as a method for operating the medical image processing apparatus.

A program according to a thirteenth aspect is a program causing a computer to implement: a function of a trainer performing additional training for a first computer-aided diagnosis device on the basis of an input medical image; a function of comparing a second computer-aided diagnosis device obtained by the additional training using the trainer with the first computer-aided diagnosis device and evaluating whether learning difference information about the additional training contributes to improvement of performance of the first computer-aided diagnosis device; a function of determining, on the basis of a result of evaluation obtained in the evaluating, whether the learning difference information is to be communicated; and a function of outputting, from a communication unit, the learning difference information in accordance with a result of determination obtained in the determining.

In the program of the thirteenth aspect, matters the same as matters specified in the second to tenth aspects can be combined as appropriate. In this case, elements of the processing units or functional units that function as means responsible for the processes and operations specified in the configuration of the apparatus can be grasped as program elements for implementing corresponding steps or functions of the processes and operations.

A medical image processing apparatus according to another aspect of the present disclosure is a medical image processing apparatus including at least one processor, the processor performing: a process of a trainer performing additional training for a first computer-aided diagnosis device on the basis of an input medical image; an evaluation process of comparing a second computer-aided diagnosis device obtained by the additional training using the trainer with the first computer-aided diagnosis device and evaluating whether learning difference information about the additional training contributes to improvement of performance of the first computer-aided diagnosis device; a communication determination process of determining, on the basis of a result of evaluation in the evaluation process, whether the learning difference information is to be communicated; and a communication process of outputting the learning difference information in accordance with a result of determination in the communication determination process.

According to the present invention, the volume of communication can be reduced, and good-quality learning data can be efficiently collected. Further, according to the present invention, the processing load of retraining or additional training performed in the machine learning apparatus using learning data collected from the medical image processing apparatus can be reduced.

DESCRIPTION OF THE PREFERRED EMBODIMENTS

Hereinafter, preferred embodiments of the present invention will be described in detail with reference to the attached drawings.

First Embodiment

Figure 1:
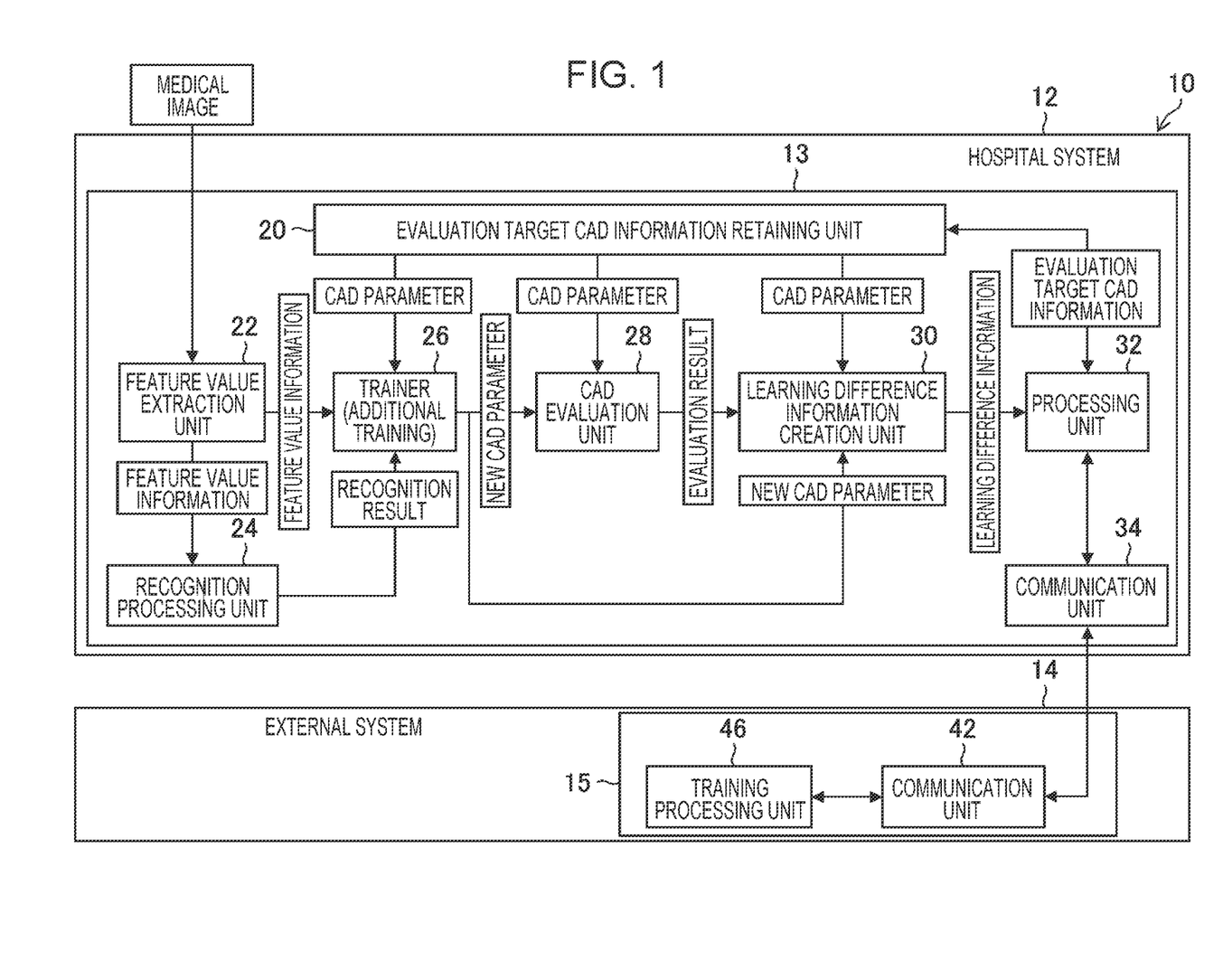
FIG. 1 is a block diagram schematically illustrating the functions of a machine learning system including a medical image processing apparatus according to a first embodiment.

FIG. 1 is a block diagram schematically illustrating the overall configuration of a machine learning system including a medical image processing apparatus according to a first embodiment. A machine learning system 10 is an information processing system that collects new learning data contributing to improvement of the performance of an existing CAD module and performs a training process of retraining or additional training for the existing CAD module by using the collected learning data and a process for creating a new CAD module having an improved performance higher than that of the existing CAD module.

The "performance of a CAD module" means the recognition accuracy or diagnosis accuracy of the CAD module. The performance of a CAD module may be expressed as "CAD performance". The existing CAD module is an example of "first computer-aided diagnosis device" and an example of "first recognizer".

The existing CAD module is a trained model that attains recognition performance by already performed machine learning. The trained model for performing a recognition process is called "recognition model". Training performed for attaining initial recognition performance of the existing CAD module is called "first training". A learning dataset used in the first training for the existing CAD module is called "first learning dataset". The first learning dataset may be a learning dataset provided in advance.

The machine learning system 10 includes a hospital system 12 and an external system 14. The hospital system 12 includes a medical image processing apparatus 13 that is an edge device installed in a hospital. Note that the term "hospital" covers the concepts of hospitals, clinics, medical examination facilities, and any other similar medical institutions. The external system 14 includes an information processing apparatus 15 that is installed in a facility outside the hospital. The medical image processing apparatus 13 and the information processing apparatus 15 are connected to each other via a communication line. Note that the communication line is not illustrated in FIG. 1.

The medical image processing apparatus 13 can be formed of one or more computers. The functions of the medical image processing apparatus 13 are outlined. The medical image processing apparatus 13 obtains data of a medical image captured by using a medical image capturing apparatus not illustrated and performs additional training by using feature value information extracted from the obtained medical image. The medical image processing apparatus 13 evaluates the result of additional training and, on the basis of the evaluation result, selectively communicates to the external system 14 learning information that truly contributes to improvement of the performance of a CAD module.

The medical image capturing apparatus is, for example, an endoscope, an X-ray imaging apparatus, a CT imaging apparatus, an MRI (magnetic resonance imaging) apparatus, a nuclear medicine diagnosis apparatus, or a fundus camera, or a combination thereof. In this embodiment, a description is given of an example case where, for example, an endoscopic image that is captured by using an endoscope is assumed to be a medical image. The medical image processing apparatus 13 in this case may be a processor device connected to the endoscope, an image importing terminal that collects data of medical images from the processor device, or an image information management device.

The medical image processing apparatus 13 includes an evaluation target CAD information retaining unit 20, a feature value extraction unit 22, a recognition processing unit 24, a trainer 26, a CAD evaluation unit 28, a learning difference information creation unit 30, a processing unit 32, and a communication unit 34.

The evaluation target CAD information retaining unit 20 is a storage device that retains evaluation target CAD information. The evaluation target CAD information is information about a CAD module that is a target of comparative evaluation with a CAD module for which additional training has been performed by using the trainer 26. The evaluation target CAD information includes parameter information about the existing CAD module. A parameter of a processing algorithm in the CAD module is an example of the parameter information. The parameter information for identifying the details of the CAD module is called a CAD parameter. The CAD parameter includes, for example, the weight of the connection between nodes in a model of a neural network and the biases of nodes.

The evaluation target CAD information retaining unit 20 is formed of a storage device, which is, for example, a hard disk device, an optical disk, a magneto-optical disk, or a semiconductor memory, or an appropriate combination thereof. The evaluation target CAD information retaining unit 20 is an example of "first information storage unit".

The feature value extraction unit 22 performs a process for processing an input medical image and extracting a feature value. The feature value extraction unit 22 may be, for example, a lower layer of a convolutional neural network (CNN) that has been trained by machine learning. The lower layer of the CNN can be used as the feature value extraction unit 22 for extracting a feature value of an image. The feature value extraction unit 22 outputs feature value information extracted from a medical image. The feature value information may be, for example, a feature map of a plurality of channels. The feature value information extracted by the feature value extraction unit 22 is sent to the recognition processing unit 24 and to the trainer 26.

To the recognition processing unit 24, a CAD module the same as the existing CAD module is applied. The recognition processing unit 24 may be, for example, a higher layer of the CNN that performs a classification task. Alternatively, the recognition processing unit 24 may be a higher layer of a hierarchical network that performs a segmentation task. Note that the recognition processing unit 24 is not limited to a model of a neural network but may be another model, such as a support vector machine (SVM), for which performance can be improved by training.

The recognition processing unit 24 performs, on the basis of the feature value information extracted by the feature value extraction unit 22, a recognition process, such as a classification task or a segmentation task, and outputs the result of recognition. The result of recognition by the recognition processing unit 24 is input to the trainer 26.

The trainer 26 includes a learning model and uses the feature value information obtained from the feature value extraction unit 22 and the recognition result obtained from the recognition processing unit 24 as learning data to perform additional training for the learning model. The learning model may be the same as that of the recognition processing unit 24 and may be shared with the recognition processing unit 24. The learning model may be a model the same as the existing CAD module in an initial state. In the learning model of the trainer 26, a parameter is updated by performing additional training.

That is, additional training is performed by using the trainer 26, and the learning model is updated to a new CAD parameter. Note that the trainer 26 may perform batch training or online training. The new CAD parameter created by the trainer 26 is called "new CAD parameter". The new CAD parameter created by the trainer 26 is sent to the CAD evaluation unit 28. A CAD module identified by using the new CAD parameter is an example of "second computer-aided diagnosis device" and an example of "second recognizer".

The CAD evaluation unit 28 compares the performance of the CAD module after training identified by using the new CAD parameter trained by the trainer 26 with the performance of the existing CAD module identified by using a CAD parameter retained in the evaluation target CAD information retaining unit 20 and evaluates whether information used in the additional training by the trainer 26 contributes to improvement of CAD performance. As an indicator for evaluating model performance by the CAD evaluation unit 28, one of the publicly known indicators, typical examples of which include "sensitivity", "specificity", and "accuracy", or a combination thereof can be used. The result of evaluation by the CAD evaluation unit 28 is sent to the learning difference information creation unit 30. The CAD evaluation unit 28 is an example of "evaluation unit".

The learning difference information creation unit 30 determines, in accordance with the evaluation result output from the CAD evaluation unit 28, whether learning difference information is to be transmitted to the external system 14, that is, determines whether communication is to be performed. In a case where the learning difference information creation unit 30 determines that transmission is to be performed, the learning difference information creation unit 30 creates learning difference information for communication. The learning difference information creation unit 30 is an example of "communication determination unit" that determines whether communication is to be performed. Note that the CAD evaluation unit 28 may include the function of communication determination.

Here, the "learning difference information" means information with which a "difference" between a CAD module before training and a CAD module after training can be reproduced. That is, the learning difference information is information based on which a "difference" between the existing CAD module before training and a new CAD module after training is generated.

The concept of the term "learning difference information" covers forms 1 to 4 illustrated below.

[Form 1] Learning difference information may be parameter difference information that indicates a difference between the existing CAD parameter before training and the new CAD parameter after training, that is, a change. Under the condition that the existing CAD parameter is known, the new CAD module after training can be reproduced as long as the parameter difference information is available.

[Form 2] Learning difference information may be the new CAD parameter itself after training. As long as the new CAD parameter is available, the new CAD module after training can be reproduced.

[Form 3] Learning difference information may be the feature value information that is used in additional training by the trainer 26 as input. When the feature value information, which is learning data used in the additional training, is used to perform a training process as in the trainer 26, the new CAD module after training similar to the result of training by the trainer 26 can be reproduced.

[Form 4] Learning difference information may be a set of original medical images from which pieces of feature value information that are used in additional training by the trainer 26 as input are extracted. When a process the same as that performed by the feature value extraction unit 22 is performed for the medical images, pieces of feature value information can be created from the medical images. Therefore, a set of pieces of feature value information similar to that in [Form 3] described above can be reproduced, and further, the new CAD module after training as in the trainer 26 can be reproduced.

Among [Form 1] to [Form 4] illustrated above, a form with which the volume of communication is smallest is [Form 1]. The volume of communication tends to increase in the order of [Form 1], [Form 2], [Form 3], and [Form 4]. In the first embodiment, learning difference information of [Form 1] is used.

That is, the learning difference information creation unit 30 illustrated in FIG. 1 creates parameter difference information, which is learning difference information indicating a difference between the existing CAD parameter read from the evaluation target CAD information retaining unit 20 and the new CAD parameter obtained from the trainer 26. The learning difference information created by the learning difference information creation unit 30 is sent to the processing unit 32. The combination of the learning difference information creation unit 30 and the processing unit 32 functions as a learning data creation unit.

The processing unit 32 is a communication signal processing unit performing signal conversion that is in conformity with the communication form of the communication unit 34. The processing unit 32 can obtain the evaluation target CAD information from the evaluation target CAD information retaining unit 20. The learning difference information and the evaluation target CAD information are subjected to necessary signal conversion in the processing unit 32 and transmitted from the communication unit 34. The communication unit 34 is a communication interface and is connected to the communication line not illustrated.

The information processing apparatus 15 of the external system 14 includes a communication unit 42 and a training processing unit 46. The communication unit 42 is a communication interface similar to the communication unit 34 and is connected to the communication line not illustrated.

The training processing unit 46 performs machine learning by using learning data that includes the learning difference information collected from the medical image processing apparatus 13. The training processing unit 46 performs a process of retraining or additional training for the existing CAD module and creates a new CAD module for which CAD performance is improved.

The new CAD module created by the training processing unit 46 can be provided at an appropriate time as an updated CAD module that replaces the existing CAD module. The information processing apparatus 15 functions as a learning data collection apparatus that collects learning data. Further, the information processing apparatus 15 functions as a machine learning apparatus that performs machine learning by using the collected learning data. Note that the first training for creating the existing CAD module may be performed by using the training processing unit 46 or by using another machine learning apparatus not illustrated.

Description of Medical Image Processing Method performed by Medical Image Processing Apparatus 13

Figure 2:
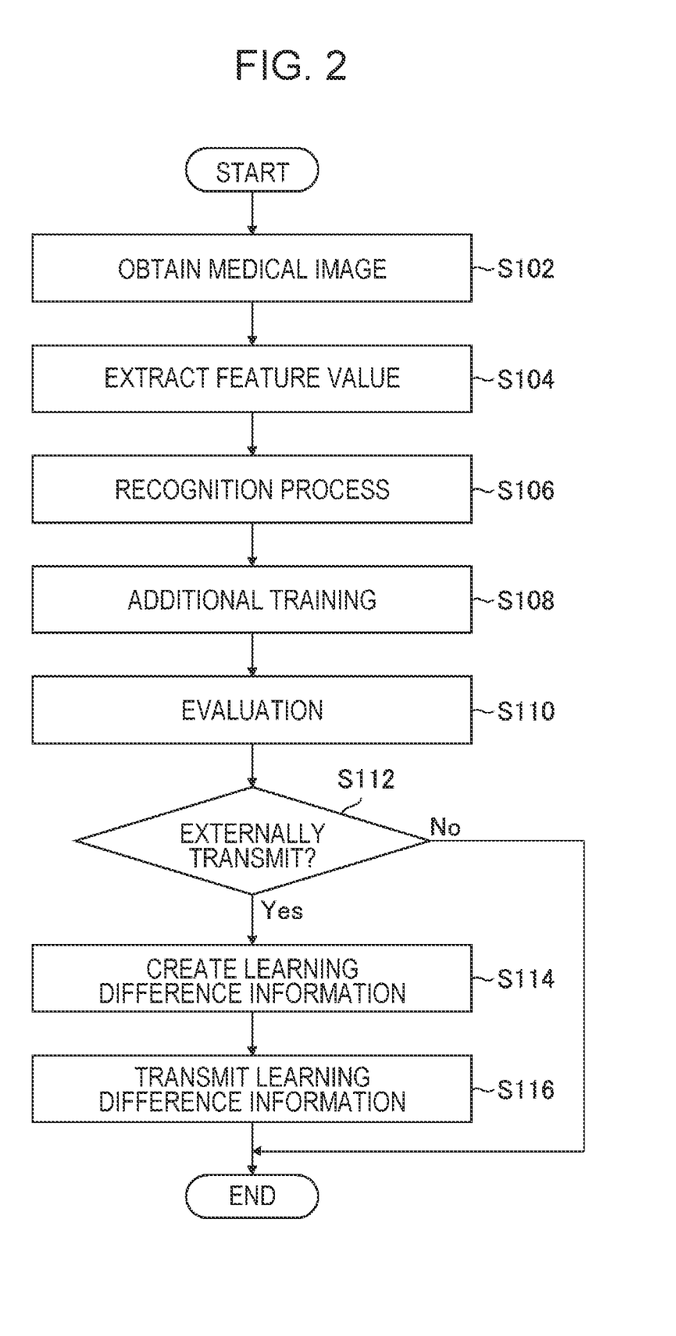
FIG. 2 is a flowchart illustrating example operations of the medical image processing apparatus.

FIG. 2 is a flowchart illustrating example operations of the medical image processing apparatus 13. The steps illustrated in FIG. 2 are performed by a computer that constitutes the medical image processing apparatus 13 in accordance with a program.

In step S102, the medical image processing apparatus 13 obtains a medical image.

In step S104, the medical image processing apparatus 13 extracts a feature value from the obtained medical image to create feature value information. The feature value information output by the feature value extraction unit 22 of the medical image processing apparatus 13 is used as input to additional training.

In step S106, the medical image processing apparatus 13 uses the feature value information to perform a recognition process. The recognition processing unit 24 of the medical image processing apparatus 13 outputs the result of recognition based on the input feature value information.

In step S108, the medical image processing apparatus 13 uses the feature value information and the recognition result to perform additional training for the existing CAD module. When the trainer 26 of the medical image processing apparatus 13 performs additional training, a new CAD parameter is created.

In step S110, the medical image processing apparatus 13 compares a new CAD module obtained by additional training with the existing CAD module to evaluate CAD performance. The CAD evaluation unit 28 of the medical image processing apparatus 13 evaluates whether information used in the additional training contributes to improvement of CAD performance.

In step S112, the medical image processing apparatus 13 performs, on the basis of the evaluation result in step S110, communication determination as to whether learning difference information is to be externally transmitted.

In a case where the result of determination in step S112 is Yes, that is, in a case where it is determined that learning difference information is to be externally transmitted, the flow proceeds to step S114.

In step S114, the medical image processing apparatus 13 creates learning difference information that is to be externally output.

In step S114, the medical image processing apparatus 13 transmits the created learning difference information.

On the other hand, in a case where the result of determination in step S112 is No, that is, in a case where it is determined that learning difference information need not to be externally transmitted, the medical image processing apparatus 13 skips the processes in step S114 and step S116, and the flowchart in FIG. 2 ends.

Figure 3:
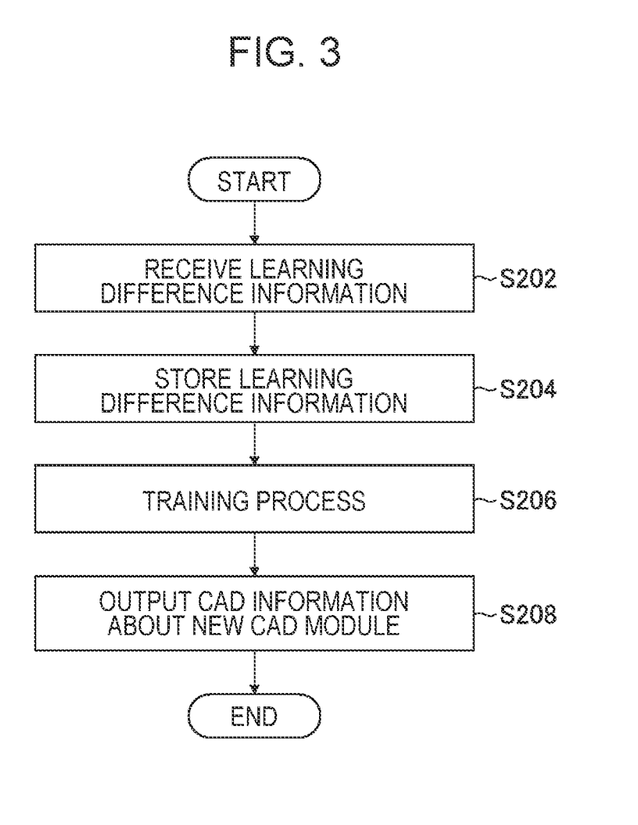
FIG. 3 is a flowchart illustrating example operations of an information processing apparatus of an external system.

FIG. 3 is a flowchart illustrating example operations of the information processing apparatus 15 of the external system 14. The steps illustrated in FIG. 3 are performed by a computer that constitutes the information processing apparatus 15 in accordance with a program.

In step S202, the information processing apparatus 15 receives learning difference information via the communication unit 42.

In step S204, the information processing apparatus 15 stores the received learning difference information. The information processing apparatus 15 includes a storage device, and the learning difference information received from the medical image processing apparatus 13 is stored in the storage device.

In step S206, the information processing apparatus 15 uses the learning difference information received from the medical image processing apparatus 13 as learning data to perform a training process. The training processing unit 46 of the information processing apparatus 15 uses the learning difference information to perform retraining or additional training for the existing CAD module. Note that the training processing unit 46 may use the first learning dataset used when the existing CAD module is created in addition to the learning difference information. The training process in step S206 may be batch training or online training. As a result of the training process in step S206, a new CAD module for which CAD performance is improved is created.

In step S208, the information processing apparatus 15 outputs CAD information about the created new CAD module. Examples of the form of "output" of CAD information include a form in which data is transmitted via the communication unit 42 and a form in which data is output in order to store the CAD information in an external storage device.

The CAD information about the new CAD module created by the information processing apparatus 15 may be transmitted to the medical image processing apparatus 13, and the "existing CAD module" may be replaced by the new CAD module to update the "existing CAD module". The CAD information about the new CAD module output from the information processing apparatus 15 can be "evaluation target CAD information" in the medical image processing apparatus 13.

The CAD information about the new CAD module created by the information processing apparatus 15 can be stored in an external storage device and distributed from the external storage device.

After step S208, the flowchart in FIG. 3 ends.

According to the first embodiment thus configured, the volume of communication between the medical image processing apparatus 13 and the information processing apparatus 15 can be reduced, and the load of the training process in the information processing apparatus 15 can be reduced.

Second Embodiment

Figure 4:
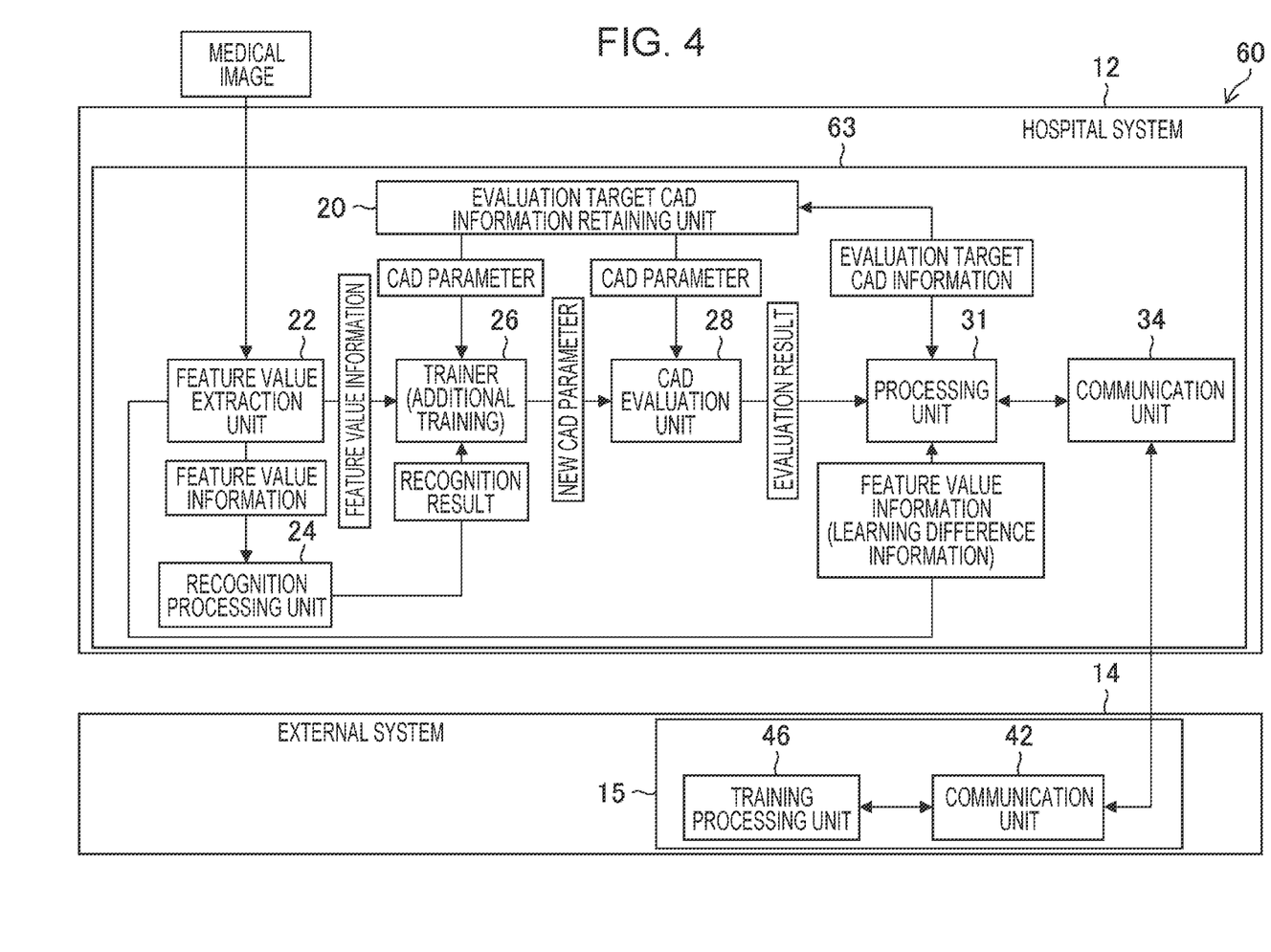
FIG. 4 is a block diagram schematically illustrating the functions of a machine learning system including a medical image processing apparatus according to a second embodiment.

FIG. 4 is a block diagram schematically illustrating the overall configuration of a machine learning system including a medical image processing apparatus according to a second embodiment. In FIG. 4, an element the same as or similar to that in the configuration illustrated in FIG. 1 is assigned the same reference numeral, and a duplicated description thereof is omitted. Differences from FIG. 1 are described.

A machine learning system 60 illustrated in FIG. 4 includes a medical image processing apparatus 63 instead of the medical image processing apparatus 13 described with reference to FIG. 1. The medical image processing apparatus 63 according to the second embodiment uses feature value information described in [Form 3] as learning difference information. That is, the medical image processing apparatus 63 transmits feature value information to the information processing apparatus 15 of the external system 14 as learning difference information.

The medical image processing apparatus 63 includes a processing unit 31 instead of the learning difference information creation unit 30 and the processing unit 32 illustrated in FIG. 1. The processing unit 31 illustrated in FIG. 4 performs communication determination regarding feature value information on the basis of the result of evaluation by the CAD evaluation unit 28. In a case where it is determined, as a result of the communication determination, that the feature value information is information that is to be transmitted, the processing unit 31 sends the feature value information output from the feature value extraction unit 22 to the communication unit 34. The processing unit 31 is an example of "communication determination unit". The other configurations and operations are similar to those in the first embodiment.

Third Embodiment

Figure 5:
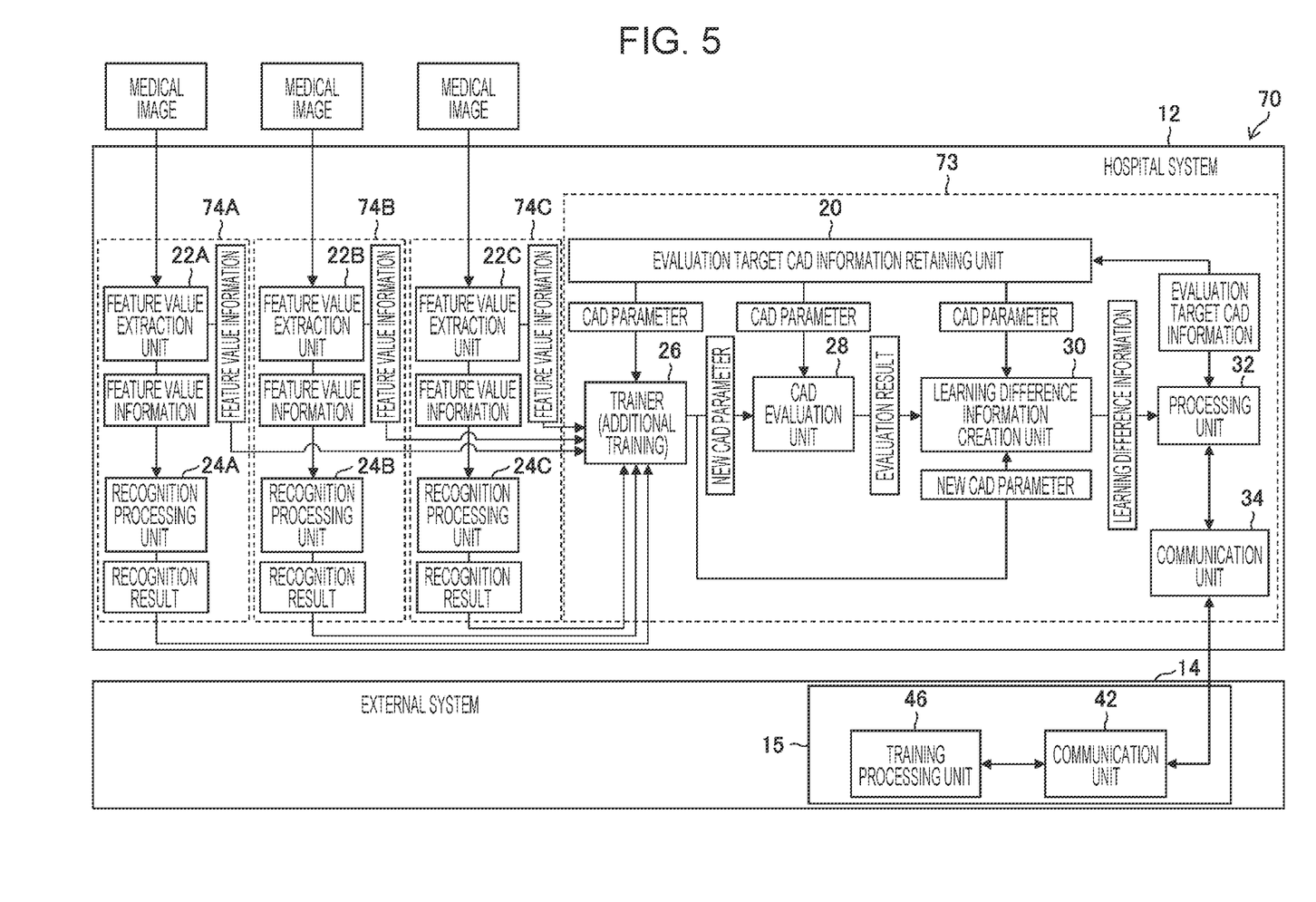
FIG. 5 is a block diagram schematically illustrating the functions of a machine learning system including a medical image processing apparatus according to a third embodiment.

FIG. 5 is a block diagram schematically illustrating the overall configuration of a machine learning system including a medical image processing apparatus according to a third embodiment. In FIG. 5, an element the same as or similar to that in the configuration illustrated in FIG. 1 is assigned the same reference numeral, and a duplicated description thereof is omitted. Differences from FIG. 1 are described.

A machine learning system 70 illustrated in FIG. 5 includes a medical image processing apparatus 73 instead of the medical image processing apparatus 13 described with reference to FIG. 1 and a plurality of devices 74A, 74B, and 74C.

The medical image processing apparatus 73 is connected to the plurality of devices 74A, 74B, and 74C. FIG. 5 illustrates three device, namely, the devices 74A, 74B, and 74C; however, the number of devices is not limited. Each of the plurality of devices 74A, 74B, and 74C may be, for example, a processor device of an endoscope. The medical image processing apparatus 73 may be, for example, a data collection system or a data management system that collects data from the plurality of processor devices.

The device 74A includes a feature value extraction unit 22A and a recognition processing unit 24A. The device 74B includes a feature value extraction unit 22B and a recognition processing unit 24B. The device 74C includes a feature value extraction unit 22C and a recognition processing unit 24C.

The feature value extraction units 22A, 22B, and 22C each have a configuration similar to that of the feature value extraction unit 22 described with reference to FIG. 1. The recognition processing units 24A, 24B, and 24C each have a configuration similar to that of the recognition processing unit 24 described with reference to FIG. 1.

The medical image processing apparatus 73 includes the evaluation target CAD information retaining unit 20, the trainer 26, the CAD evaluation unit 28, the learning difference information creation unit 30, the processing unit 32, and the communication unit 34.

The trainer 26 obtains feature value information and a recognition result from each of the devices 74A, 74B, and 74C and creates new CAD parameters.

The CAD evaluation unit 28 evaluates the plurality of new CAD parameters created by using respective pieces of information obtained from the plurality of devices 74A, 74B, and 74C and selectively sets a new CAD parameter having a good evaluation result as a transmission target. For example, among the plurality of new CAD parameters, the CAD evaluation unit 28 may selectively set only one CAD parameter having the top performance or only the top two CAD parameters as a transmission target or transmission targets. The other configurations are similar to those in the first embodiment.

First Modification

In the first to third embodiments, an example has been described where the medical image processing apparatus, which is an edge device of the hospital system 12, and the information processing apparatus of the external system 14 are connected to each other on a one-to-one basis; however, a plurality of medical image processing apparatuses (edge devices) may be connected to the information processing apparatus of the external system 14 on a many-to-one basis.

Figure 6:
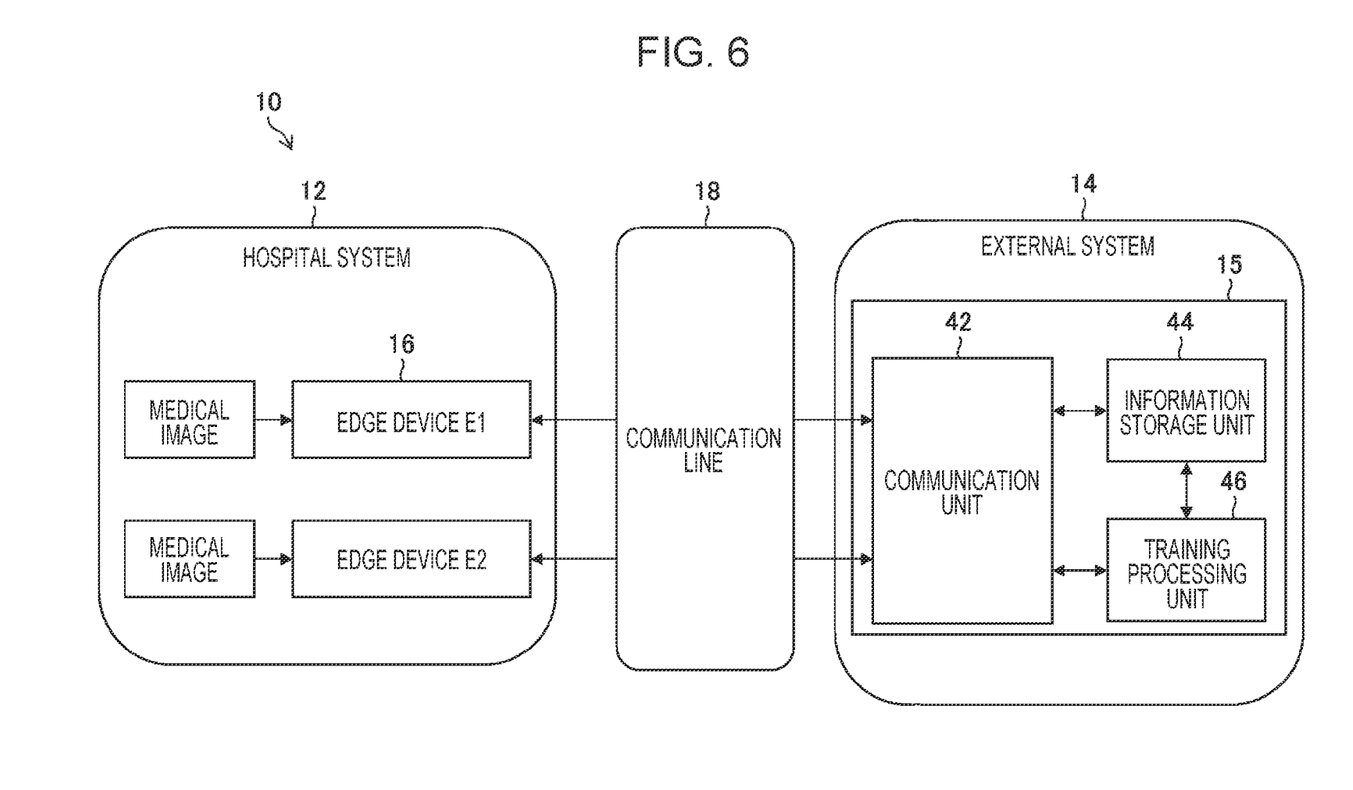
FIG. 6 is a block diagram illustrating another example form of the machine learning system.

FIG. 6 illustrates another example form of the machine learning system. FIG. 6 is a block diagram illustrating an example where a plurality of edge devices are included in the hospital system 12. In FIG. 6, an element the same as or similar to that illustrated in FIG. 1 is assigned the same reference numeral, and a duplicated description thereof is omitted.

The hospital system 12 includes a plurality of edge devices 16, and each edge device is connected to the external system 14 via a communication line 18. FIG. 6 illustrates two edge devices 16, which are respectively expressed as "E1" and "E2". The configuration of each edge device 16 is similar to the configuration of the medical image processing apparatus 13 in FIG. 1.

The information processing apparatus 15 of the external system 14 includes an information storage unit 44. The information storage unit 44 is formed of a storage device, which is, for example, a hard disk device, an optical disk, a magneto-optical disk, or a semiconductor memory, or an appropriate combination thereof. The information storage unit 44 is an example of "second information storage unit". The information storage unit 44 may retain the first learning dataset used in the first training.

Information obtained via the communication unit 42 is saved in the information storage unit 44. New CAD information created by the training processing unit 46 is saved in the information storage unit 44.

Second Modification

Figure 7:
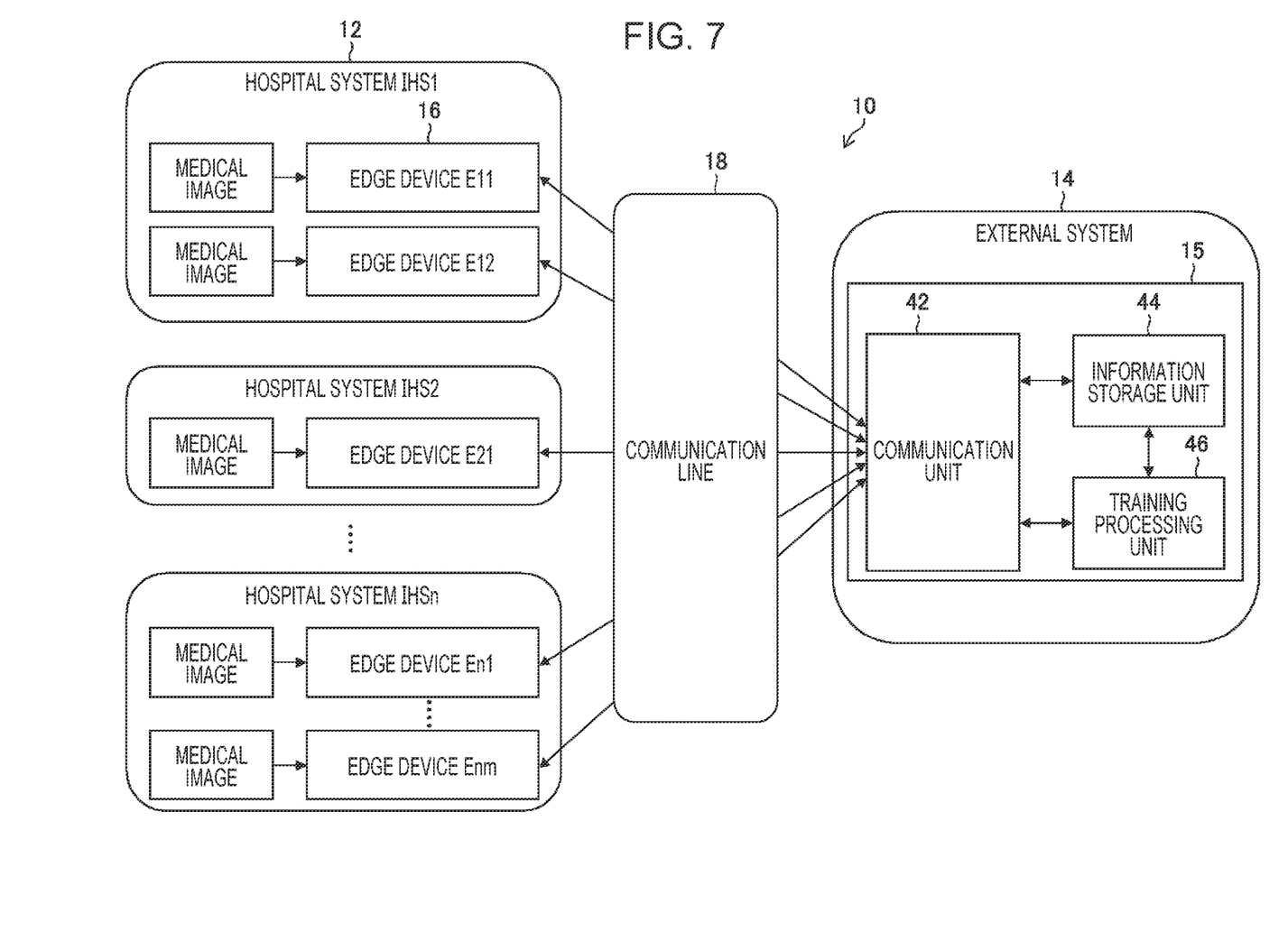
FIG. 7 is a block diagram schematically illustrating the machine learning system formed of a combination of a plurality of hospital systems and one external system.

FIG. 7 is a block diagram schematically illustrating the machine learning system formed of a combination of a plurality of hospital systems and one external system. In FIG. 7, an element the same as or similar to that illustrated in FIG. 1 or FIG. 6 is assigned the same reference numeral, and a duplicated description thereof is omitted.

As illustrated in FIG. 7, a plurality of hospital systems 12 and one external system 14 may be connected to each other on a many-to-one basis. As described with reference to FIG. 6, each of the hospital systems 12 includes one or more edge devices. In FIG. 7, the plurality of hospital systems 12 are expressed as "IHS1", "IHS2", . . . , "IHSn".

The edge devices 16 included in the hospital systems 12 are expressed as "E11", "E12", "E21", "En1", and "Enm", where "n" is an index number for identifying one hospital system 12 and "m" is an index number for identifying one edge device 16 in one hospital system 12.

With the configuration illustrated in FIG. 7, good-quality learning data can be efficiently collected from a large number of edge devices 16, and a large amount of learning data can be obtained.

Hardware Configuration of Processing Units and Control Unit

The hardware configuration of the processing units, which are, for example, the feature value extraction unit 22, the recognition processing unit 24, the trainer 26, the CAD evaluation unit 28, the learning difference information creation unit 30, the processing units 31 and 32, the communication units 34 and 42, and the training processing unit 46 described in the embodiments and which perform various types of processing, is implemented as various processors as described below.

The various processors include a CPU (central processing unit), which is a general-purpose processor executing a program to function as various processing units, a GPU (graphics processing unit), which is a processor specialized in image processing, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or two or more processors of the same type or different types. For example, one processing unit may be configured as a plurality of FPGAs, a combination of a CPU and an FPGA, or a combination of a CPU and a GPU. Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in which circuit elements, such as semiconductor elements, are combined.

Example Hardware Configuration of Computer

Figure 8:
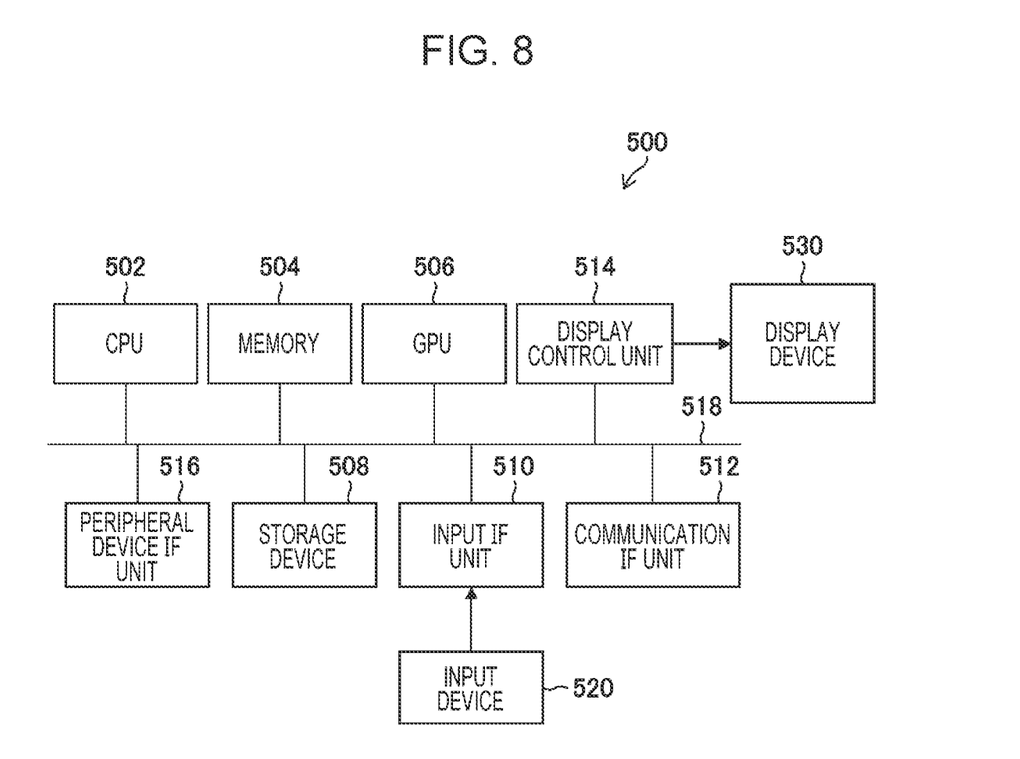
FIG. 8 is a block diagram illustrating an example hardware configuration of a computer.

FIG. 8 is a block diagram illustrating an example hardware configuration of a computer that can be used as an apparatus for implementing some or all of the functions of the medical image processing apparatus and the information processing apparatus. The computer may be of a desktop type, a laptop type, a tablet type, or any other type. The computer may be a server computer or a microcomputer.

A computer 500 includes a CPU 502, a memory 504, a GPU 506, a storage device 508, an input interface unit 510, a communication interface unit 512 for network connection, a display control unit 514, a peripheral device interface unit 516, and a bus 518. In FIG. 8, the expression "IF" means "interface".

The storage device 508 may be formed of, for example, a hard disk device. In the storage device 508, for example, various programs and data necessary for image processing, such as the training process and/or the recognition process, are stored. When a program stored in the storage device 508 is loaded to the memory 504 and executed by the CPU 502, the computer functions as means for performing various types of processing defined by the program.

An input device 520 is connected to the input interface unit 510. The input device 520 may be, for example, an operation button or a keyboard, a mouse, a touch panel, or a voice input device, or an appropriate combination thereof. A user can operate the input device 520 to input various instructions.

A display device 530 is connected to the display control unit 514. The display device 530 may be, for example, a liquid crystal display, an organic EL (organic electroluminescence: OEL) display, or a projector, or an appropriate combination thereof.

Program for Operating Computer

A program for causing a computer to implement the processing functions of the medical image processing apparatus and at least one of the learning data collection function or the training function of the information processing apparatus described in the above embodiments can be recorded to a computer-readable medium, such as an optical disk, a magnetic disk, a semiconductor memory, or any other non-transitory tangible information storage medium, and the program can be provided via the information storage medium. Instead of the form in which the program is stored in such a non-transitory tangible information storage medium and provided, a telecommunication line, such as the Internet, can be used to provide a program signal as a download service.

Combination of Embodiments, Modifications, etc.

Components described in the above embodiments and components described in the above modifications can be combined as appropriate, and some of the components can be replaced.

For example, the medical image processing apparatus 13 may transmit parameter difference information and feature value information to the external system 14. The medical image processing apparatus 13 may transmit a new CAD parameter and feature value information to the external system 14.

Others

In the embodiments of the present invention described above, any configuration requirement can be changed, added, or deleted as appropriate without departing from the spirit of the present invention. The present invention is not limited to the above-described embodiments, and modifications can be made by a person having ordinary skill in the equivalent related art within the technical scope of the present invention.

REFERENCE SIGNS LIST 10 machine learning system
12 hospital system
13 medical image processing apparatus
14 external system
15 information processing apparatus
16 edge device
18 communication line
20 evaluation target CAD information retaining unit
22, 22A, 22B, 22C feature value extraction unit
24, 24A, 24B, 24C recognition processing unit
26 trainer
28 CAD evaluation unit
30 learning difference information creation unit
31, 32 processing unit
34, 42 communication unit
44 information storage unit
46 training processing unit
60 machine learning system
63 medical image processing apparatus
70 machine learning system
73 medical image processing apparatus
74A, 74B, 74C device
500 computer
502 CPU
504 memory
506 GPU
508 storage device
510 input interface unit
512 communication interface unit
514 display control unit
516 peripheral device interface unit
518 bus
520 input device
530 display device
S102 to S116 steps of processes performed by medical image processing apparatus
S202 to S208 steps of processes performed by information processing apparatus

What is claimed is:

1. A medical image processing apparatus comprising one or more first processors configured to:
   perform additional training for a first computer-aided diagnosis device on a basis of an input medical image;
   compare a second computer-aided diagnosis device obtained by the additional training with the first computer-aided diagnosis device and evaluate whether learning difference information about the additional training contributes to improvement of performance of the first computer-aided diagnosis device;
   determine, on a basis of a result of the evaluation, whether the learning difference information is to be communicated; and
   perform communication to output the learning difference information in accordance with a result of the determination.

2. The medical image processing apparatus according to claim 1, wherein the one or more first processors are further configured to:
   extract feature value information about the medical image;
   perform a recognition process on a basis of the feature value information, wherein information; and
   perform the additional training on a basis of the feature value information and a result of the recognition process.

3. The medical image processing apparatus according to claim 1, further comprising a first memory configured to store parameter information about the first computer-aided diagnosis device.

4. The medical image processing apparatus according to claim 1, wherein the learning difference information includes parameter difference information that indicates a difference between parameter information about the first computer-aided diagnosis device and parameter information about the second computer-aided diagnosis device.

5. The medical image processing apparatus according to claim 1, wherein the learning difference information includes parameter information about the second computer-aided diagnosis device.

6. The medical image processing apparatus according to claim 2, wherein the learning difference information includes the feature value information.

7. The medical image processing apparatus according to claim 1, wherein the learning difference information includes the medical image provided for the additional training.

8. The medical image processing apparatus according to claim 1, wherein
the first computer-aided diagnosis device is a first recognizer that is created in advance by performing machine learning using a first learning dataset, and
the second computer-aided diagnosis device is a second recognizer for which a parameter of the first recognizer is changed.

9. A machine learning system comprising:
the medical image processing apparatus according to claim 1; and
an information processing apparatus including one or more second processors configured to receive the learning difference information output from the medical image processing apparatus to collect learning data including the learning difference information.

10. The machine learning system according to claim 9, wherein the one or more second processors are configured to use the received learning difference information to perform a training process for the first computer-aided diagnosis device.

11. The machine learning system according to claim 9, wherein the information processing apparatus further includes a second memory configured to store the received learning difference information.

12. A medical image processing method to be performed by a medical image processing apparatus, the medical image processing method comprising:
a step of obtaining a medical image;
a step of performing additional training for a first computer-aided diagnosis device by using a trainer on a basis of the obtained medical image;
a step of comparing a second computer-aided diagnosis device obtained by the additional training using the trainer with the first computer-aided diagnosis device and evaluating whether learning difference information about the additional training contributes to improvement of performance of the first computer-aided diagnosis device;
a step of determining, on a basis of a result of evaluation obtained in the evaluating, whether the learning difference information is to be communicated; and
a step of outputting, from a communication unit, the learning difference information in accordance with a result of determination obtained in the determining.

13. A storage medium that is a non-transitory computer-readable storage medium and that, in a case where a command stored in the storage medium is read by a computer, causes the computer to execute:
a function of a trainer performing additional training for a first computer-aided diagnosis device on a basis of an input medical image;
a function of comparing a second computer-aided diagnosis device obtained by the additional training using the trainer with the first computer-aided diagnosis device and evaluating whether learning difference information about the additional training contributes to improvement of performance of the first computer-aided diagnosis device;
a function of determining, on a basis of a result of evaluation obtained in the evaluating, whether the learning difference information is to be communicated; and
a function of outputting, from a communication unit, the learning difference information in accordance with a result of determination obtained in the determining.

* * * * *